US011737917B2

(12) United States Patent
Koh et al.

(10) Patent No.: US 11,737,917 B2
(45) Date of Patent: Aug. 29, 2023

(54) SYSTEM AND APPARATUS FOR EYE DROP ADMINISTRATION COMPLIANCE

(71) Applicants: NATIONAL UNIVERSITY HOSPITAL (SINGAPORE) PTE LTD, Singapore (SG); NATIONAL UNIVERSITY OF SINGAPORE, Singapore (SG)

(72) Inventors: Victor Teck Chang Koh, Singapore (SG); Muhammad Azri Bin Razali, Singapore (SG); Teri Danielle You Ying Yeoh, Singapore (SG); Min Li Tey, Singapore (SG); Hui Chen Charmaine Chai, Singapore (SG); Yien Lai, Singapore (SG)

(73) Assignees: NATIONAL UNIVERSITY HOSPITAL (SINGAPORE) PTE LTD, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 656 days.

(21) Appl. No.: 16/639,131

(22) PCT Filed: Aug. 17, 2018

(86) PCT No.: PCT/SG2018/050418
§ 371 (c)(1),
(2) Date: Feb. 14, 2020

(87) PCT Pub. No.: WO2019/035769
PCT Pub. Date: Feb. 21, 2019

(65) Prior Publication Data
US 2020/0229970 A1    Jul. 23, 2020

(30) Foreign Application Priority Data
Aug. 17, 2017    (SG) ..................... SG10201706747U (51) Int. Cl.
*A61F 9/00*    (2006.01)
*G16H 20/13*    (2018.01)

(52) U.S. Cl.
CPC ........... *A61F 9/0008* (2013.01); *G16H 20/13* (2018.01); *A61F 2250/008* (2013.01); *A61F 2250/0086* (2013.01)

(58) Field of Classification Search
CPC .......... A61F 9/0008; G16H 20/13; A61J 1/05; A61J 7/04; A61M 35/00; B65D 47/18; B05B 11/04
See application file for complete search history.

(56) References Cited

U.S. PATENT DOCUMENTS 5,135,485 A *  8/1992  Cohen ................... G01F 23/268
                                                       604/67
6,259,654 B1 * 7/2001  de la Huerga ........ A61J 7/0481
                                                        368/10
(Continued)

FOREIGN PATENT DOCUMENTS

DE       202009006230 U1    9/2010

*Primary Examiner* — Courtney B Fredrickson
(74) *Attorney, Agent, or Firm* — Soroker Agmon Nordman Pte Ltd (57) ABSTRACT

An eye drop bottle storage unit for eye drop administration compliance includes a memory, a processor, and one or a plurality of eye drop bottle pods, where each eye drop bottle pod of the one or said plurality of eye drop bottle pods is configured to hold an eye drop bottle, and comprises one or a plurality of sensors. The memory is configured to store data of an eye drop administration regime of a subject. The processor is configured to receive signals from the one or said plurality of sensors of each eye drop bottle pod, and to determine from the received signals whether the subject administered eye drops into eyes of the subject from each eye drop bottle respectively held in each eye drop bottle pod (Continued)

of the one or said plurality of eye drop bottle pods in accordance with the eye drop administration regime data.

32 Claims, 9 Drawing Sheets

(56) References Cited

U.S. PATENT DOCUMENTS

| | | |
|---|---|---|
| 2014/0236351 A1 | 8/2014 | Hyde et al. |
| 2015/0045727 A1* | 2/2015 | Bammer ............ A61M 5/31525 |
| | | 73/304 C |
| 2015/0173945 A1 | 6/2015 | Fateh |
| 2015/0289805 A1* | 10/2015 | Eaton ...................... G16H 20/13 |
| | | 604/290 |
| 2015/0359667 A1 | 12/2015 | Brue |
| 2016/0239635 A1* | 8/2016 | Fateh .................. A61M 15/008 |
| 2016/0274048 A1* | 9/2016 | Mehregany ................ A61J 1/03 |
| 2019/0295718 A1* | 9/2019 | Lawhorn ................ G16H 20/40 |

\* cited by examiner

FIG. 10

SYSTEM AND APPARATUS FOR EYE DROP ADMINISTRATION COMPLIANCE

FIELD OF THE INVENTION

The present invention relates to an eye drop administration. More specifically, the present invention relates to a system and apparatus for eye drop administration compliance.

BACKGROUND OF THE INVENTION

Many eye complications, illnesses, and/or pathologies, such as glaucoma, may be treated by the use of medications delivered to the eye, typically in the form of eye drops. Glaucoma patients, for example, are typically elderly and may face difficulties understanding, remembering, recalling, reading or recognizing medications and medication packaging. In this case, the administration of eye drops by an elderly patient, may become particularly problematic with multi-eye drop medication schemes, where the patient is unable to read and/or understand the language in which the eye drop bottles and eye drop medication instructions are printed.

These scenarios may become particularly critical in cases, for example, where high intra-ocular pressures, such as from glaucoma, require eye drop medications to be regularly applied to reduce the pressure to normal levels to prevent blindness and/or in cases where eye drops medications are needed to restore vision after eye surgery. Patients may also have to apply multiple eye drop medications, where each eye drop medication has a different eye drop dispenser shape and size. Studies have shown that the up to 80% of glaucoma patients are non-adherent to their eye drop regimes. Some patients have gone blind as a result. Failure to adhere to medication regiment or the changing thereof may occur as a result of poor physician patient communications. Non-adherence, may lead to over use of eye drops medication likely to result in wastage and often side effects.

Thus, it may be desirable to have a system and apparatus for assisting the patient in adhering and complying with complex eye drop therapeutic regimes for the management of eye illnesses and/or pathologies.

SUMMARY OF THE INVENTION

There is thus provided, in accordance with some embodiments of the present invention, an eye drop bottle storage unit for eye drop administration compliance including a memory, a processor, and one or a plurality of eye drop bottle pods, where each eye drop bottle pod of the one or said plurality of eye drop bottle pods is configured to hold an eye drop bottle, and includes one or a plurality of sensors. The memory is configured to store data of an eye drop administration regime of a subject. The processor is configured to receive signals from the one or said plurality of sensors of each eye drop bottle pod, and to determine from the received signals whether the subject administered eye drops into eyes of the subject from each eye drop bottle respectively held in each eye drop bottle pod of the one or said plurality of eye drop bottle pods in accordance with the eye drop administration regime data.

Furthermore, in accordance with some embodiments of the present invention, the one or plurality of sensors include capacitive sensors placed at predefined positions along the length of each eye drop bottle in each eye drop bottle pod, and where the processor is configured to determine whether the subject administered eye drops from each eye drop bottle by computing a height of a liquid in each eye drop bottle using capacitance measurements computed from the signals received from the capacitive ring sensors.

Furthermore, in accordance with some embodiments of the present invention, the processor is configured to compute a compliance factor and to assess whether the subject is complying with the eye drop administration regime when the compliance factor is greater than a predefined threshold.

Furthermore, in accordance with some embodiments of the present invention, the one or said plurality of sensors are selected from the group consisting of a capacitive sensor, a pressure sensor, a thermal sensor, a weight sensor, a Radio Frequency identification (RFID) tag scanner, a bar code scanner, a piezoelectric element for pressure sensing, an infrared proximity sensor, and an ultrasonic sensor.

There is further provided, in accordance with some embodiments of the present invention, a method for eye drop administration compliance including in a memory, storing data of an eye drop administration regime of a subject. In a processor, signals may be received from one or a plurality of sensors from one or plurality of eye drop bottle pods, wherein each eye drop bottle pod from the one or said plurality of eye drop bottle pods is configured to hold an eye drop bottle. The received signals may be used to determine whether the subject administered eye drops into eyes of the subject from each eye drop bottle respectively held in each eye drop bottle pod of the one or said plurality of eye drop bottle pods in accordance with the eye drop administration regime data.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Many patients, typically elderly patients, with eye complications, illnesses, and/or pathologies, such as glaucoma, for example, may be unable to read the drug name and/or instructions on the medication bottle, such as on an eye drop medication bottle used to treat the eye problem. Many patients may recognize eye drop medications from the color of the bottle.

When the patient may be elderly and/or may face difficulties understanding, remembering, recalling, reading or recognizing medications and medication packaging, and/or when the patient is unable to read and/or understand the language in which the eye drop bottles and the eye drop medication instructions are printed, failure to comply with eye-drop medication schemes as determined by the patient's health care professional, such as an ophthalmologist, may ultimately result in blindness for the patient. These issues may be further exacerbated when patients may need to use complex eye drop medication dosing schemes, for example, three different eye drops, each taken at different times of the day.

Embodiments of the present invention herein describe apparatus and a system for assisting the patient in eye drop administration compliance. An eye drop administration compliance system as described herein may include an eye drop bottle storage unit with a controller unit associated and in contact with one or a plurality of smart eye drop bottle pods configured to hold one or more eye drop medication bottles, a personalized eye drop medication card specifying the patient's eye drop medication regime, and an application typically for mobile devices to display eye drop administration compliance rates.

The terms "eye drop", "eye drops", and "eye drop medication" may be used interchangeably herein. The eye drop medication is intended to be administered or delivered to the eyes of the patient. The eye drops may be self-administered or delivered by a third party such as a health care professional, health care provider, or family member, for example.

Figure 1:
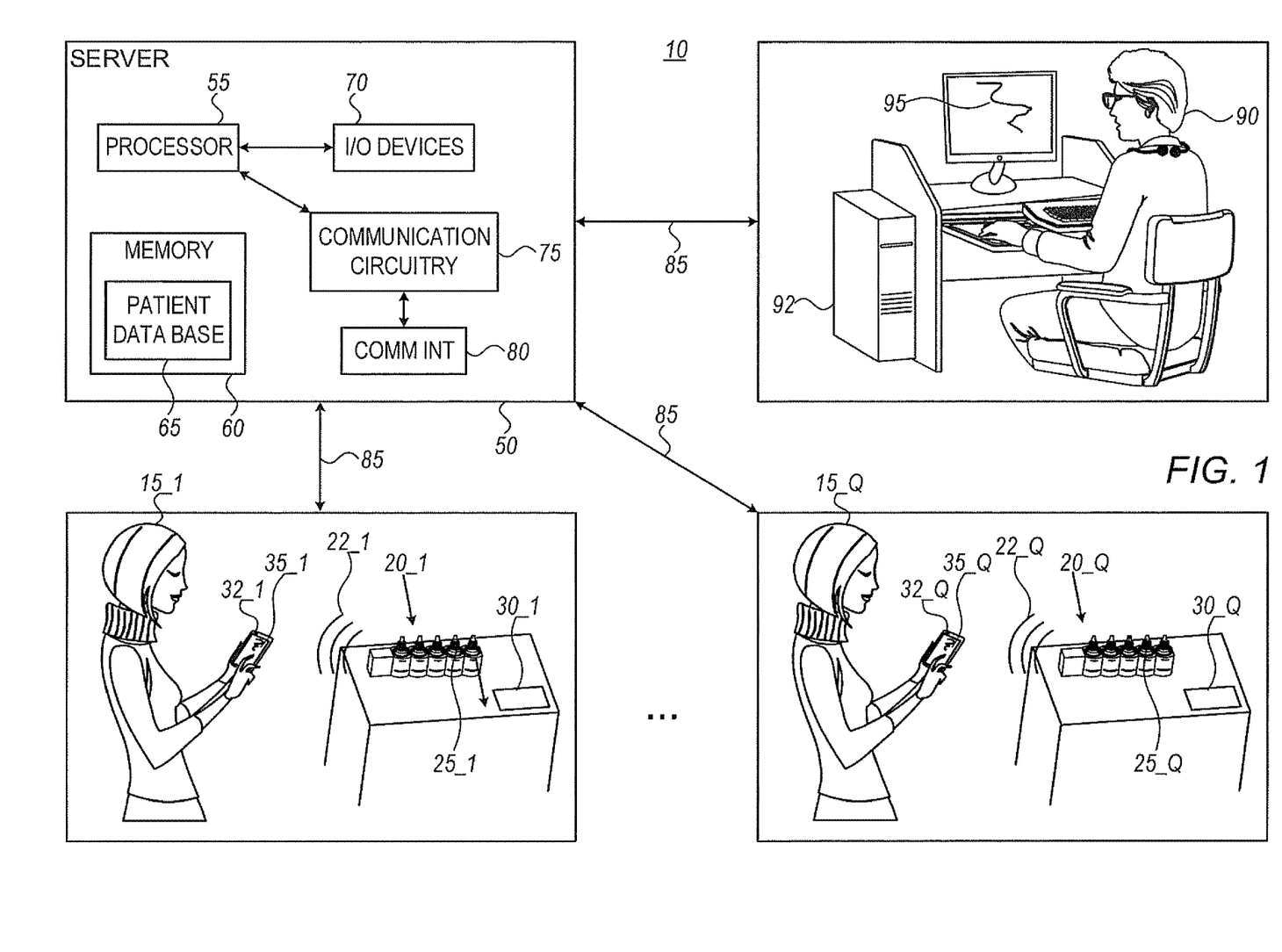
FIG. 1 schematically illustrates an eye drop administration compliance system, in accordance with some embodiments of the present invention.

FIG. 1 schematically illustrates an eye drop administration compliance system 10, in accordance with some embodiments of the present invention. Eye drop administration compliance system 10 may include one or more subjects 15_1 . . . 15_Q, typically patients, where Q is the number of subjects. Each of the one or more subjects may be required to administer eye drops as therapeutic treatments to alleviate eye illnesses such as glaucoma, for example, in accordance with an eye drop administration regime. The eye drop administration regime may require each subject 15 to apply different eye drop medications held respectively in different eye drop bottles 25 (e.g., 25_1 . . . 25_Q). Each of the eye drops bottles for each of patients 15_1 . . . 15_Q may be held and stored in an eye drop bottle storage unit 20 (e.g., 20_1 . . . 20_Q). The eye drop administration regime may be printed on a personalized eye drop medication card 30 (e.g., 30_1 . . . 30_Q).

In some embodiments of the present invention, eye drop bottle storage unit 20 (e.g., 20_1 . . . 20_Q) may be configured to send out an audio signal 22 (e.g., 22_1 . . . 22_Q) for each of patients 15_1 . . . 15_Q to prompt the patient to administer eye drops from one or more of the eye drop medications in the eye bottles held in eye drop bottle storage units 20_1 . . . 20_Q. When the patient administers the eye drop medication, eye drop bottle storage units 20_1 . . . 20_Q may be configured to detect which medications were administered and the number of eye drops used from each of the eye drop bottles. For example, eye drop bottle storage units 20_1 . . . 20_Q may be configured to detect the volume of the liquid in each of the eye drop bottles before and after the administration of the eye drop medications, where the change in the volume is related to the number of eye drops applied.

In some embodiments of the present invention, eye drop bottle storage units 20_1 . . . 20_Q may store the personalized eye drop administration regime respectively for each of patients 15_1 . . . 15_Q and may be configured to detect whether the patient is compliant in administering eye drops in accordance with the patient's personalized eye drop administration regime. A compliance factor may be defined herein as the percentage of the number of instances that the patient administers the correct number of eye drops at the proper time for a given medication located in a given eye drop bottle held in eye drop bottle storage unit 20. If multiple medications may be required by the personalized eye drop administration regime, the compliance factor is the overall percentage of the number of instances that the patient administers the correct number of eye drops of all of the patient's medications at the proper time in accordance with the eye drop administration regime.

In some embodiments of the present invention, eye drop bottle storage unit 20 may be configured to display the compliance factor on an eye drop administration compliance application 35 operating a mobile device 32, such as a smartphone. In other embodiments, eye drop administration compliance application 35 may be also configured to display the volume of the liquid remaining in each of the eye drop bottles, measured according to the height of the liquid in the eye drop bottles. In yet other embodiments, eye drop administration compliance application 35 may allow the patient to automatically reorder and refill any of the eye drop medications in the eye drop bottles stored in eye drop bottle storage unit 20 when the remaining volume of the medication in the bottle falls below a predefined threshold such as 10 or 20%, for example. In response, new eye drop medications may be delivered to the patient.

In some embodiments of the present invention, eye drop administration compliance system 10 may include a server 50 (e.g., a remote server) configured to communicate 85 with each of the one or more eye drop bottle storage units 20_1 . . . 20_Q via a communication interface 80 coupled to communication circuitry 75. Communication circuitry 75 may include circuitry to support a wired or wireless connection over a communication network to server 50 using any suitable communication protocols such as ethernet, Wireless fidelity (Wi-Fi), Bluetooth, for example.

Server 50 may also include a server processor 55, a server memory 60, and server input/output (I/O) devices 70. Eye drop administration compliance system 10 may include a database 65 stored on server 50 configured to send information to the patient about the eye drop administration regime, to receive information from eye drop bottle storage unit regarding the patient compliance in administering eye drops in accordance with the eye drop administration regime, and to report to the patient and health care professionals, using an application, about the patient's compliance with the eye drop regime.

In some embodiments of the present invention, a user 90, such as a health care professional, may be using a remote terminal 92 with display 95. Remote terminal 92 may communicate 80 with server 50. Remote terminal 92 may be operating an application or program for managing the personalized eye drop administration regimes for each of patients 15_1 . . . 15_Q and to alert user 90 as to patient compliance. In response, user 90 may update the personalized eye drop administration regimes daily or periodically as needed. In other embodiments, user 90 may be in the same location as one or more of the patients. Remote terminal 92 may include, for example, a computer, tablet, or smart phone used by user 90.

In some embodiments, eye drop administration compliance system 10 may alert both patient 15 and health care professional 90 if the patient is not adhering to the eye drop medication regime. In other embodiments, eye drop administration compliance system 10 may assess whether a particular eye drop medication in an eye drop bottle is being under-dosed or over-dosed so as to evaluate the real-time risk to the patient's vision. In yet other embodiments, eye drop administration compliance system 10 may send compliance alerts to mobile device 32, such as a smartphone of the patient.

Figure 2:
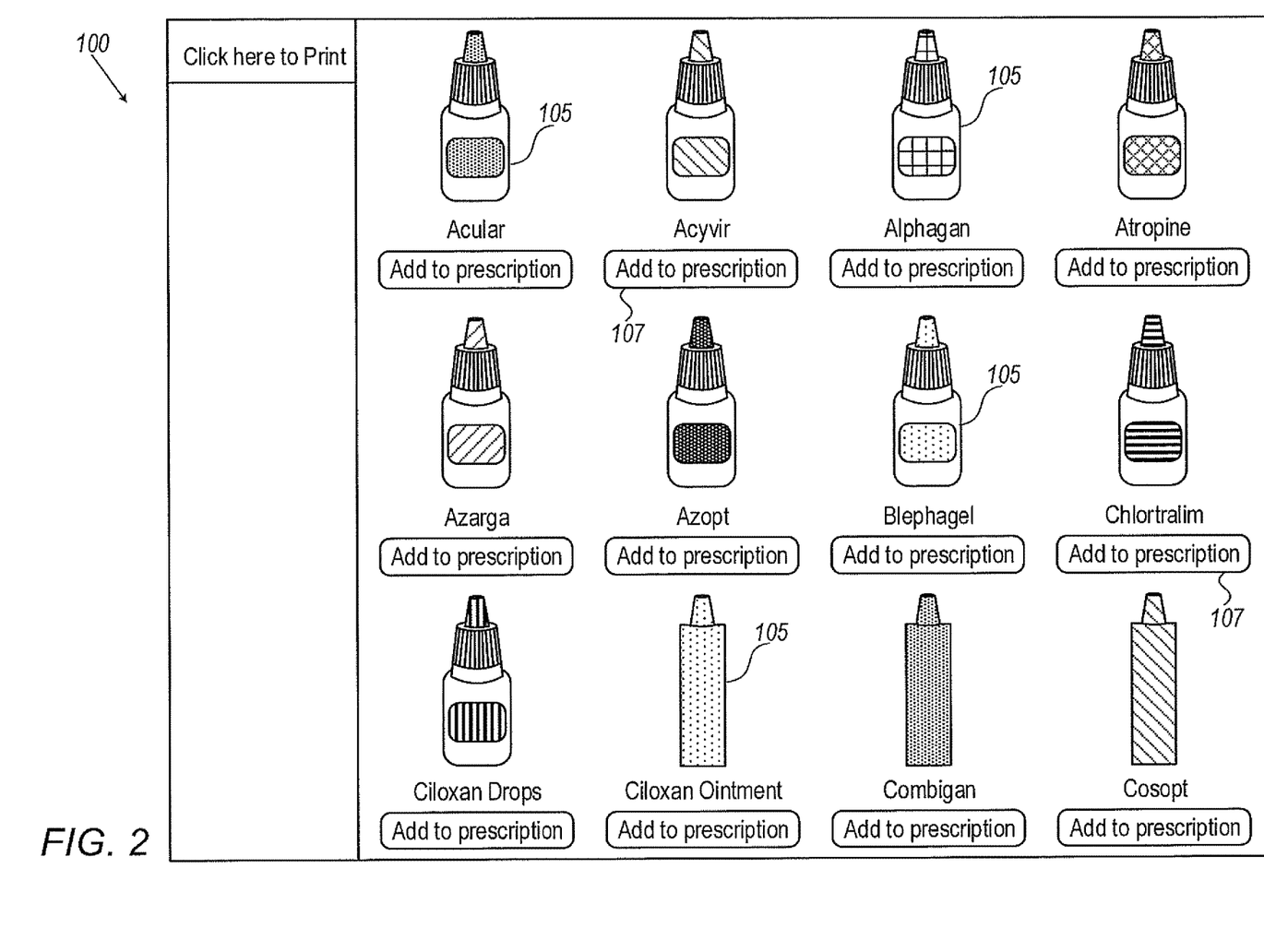
FIG. 2 schematically illustrates an exemplary graphic user interface (GUI) on a remote terminal, in accordance with some embodiments of the present invention, FIG. 3 schematically illustrates a personalized eye drop medication card, in accordance with some embodiments of the present invention.

FIG. 2 schematically illustrates an exemplary graphic user interface (GUI) 100 of on remote terminal 92, in accordance with some embodiments of the present invention. In some embodiments, GUI 100 may be part of a web application running on remote terminal 92 or remote server 50. User 90 may use the web application via GUI 100 to build or generate personalized eye drop medication card 30. User 90, for example, may choose any of eye drop medications 105 and push icon 107 "add to prescription".

In some embodiments of the present invention, the web application may be programmed using HTML5, CSS and Javascript hosted on a system using Nginx, for example. The database may be generated using MySQL.

Figure 3:
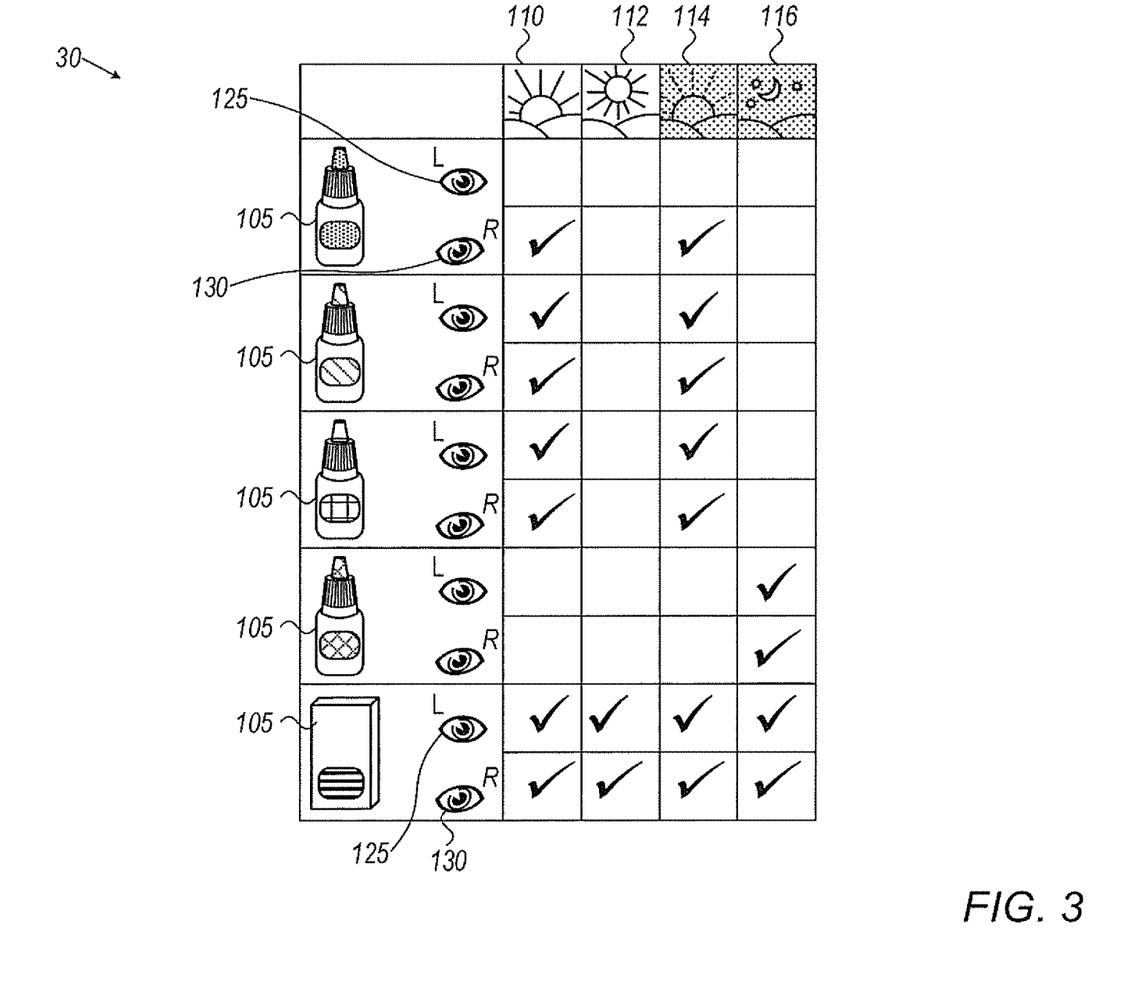

FIG. 3 schematically illustrates personalized eye drop medication card 30, in accordance with some embodiments of the present invention. Personalized eye drop medication card 30 may include medications 105 (e.g. chosen, for example, by user 90 using GUI 100). Personalized eye drop medication card 30 may use pictorial indicia to indicate the time of day (e.g., morning 110, afternoon 112, evening 114, and night 116) that the eye drop medication is to be administered, the number of eye drops, and/or whether to apply the eye drops to a right eye 125 or a left eye 130.

In some embodiments of the present invention, the web application may be used by health care professionals to update the prescriptions and medication dosages. The web application may be used to print out the personalized eye drop medication card 30 and track the subject's compliance history.

Figures 4A, 4B:
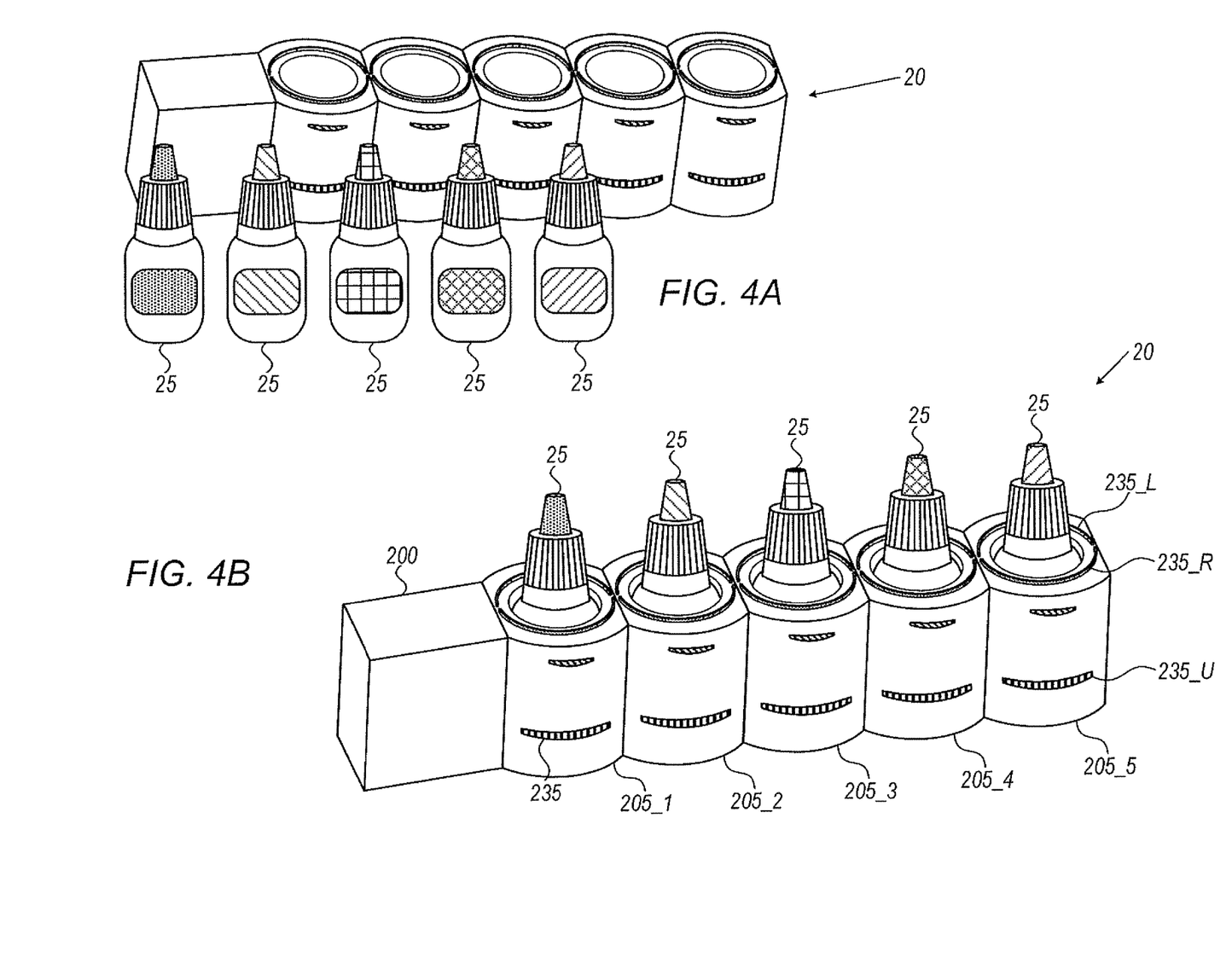
FIG. 4A schematically illustrates an eye drop bottle storage unit and eye drop medication bottles, in accordance with some embodiments of the present invention.
FIG. 4B schematically illustrates an eye drop bottle storage unit showing the eye drop medication bottles placed within eye drop bottle pods, in accordance with some embodiments of the present invention.

FIG. 4A schematically illustrates eye drop bottle storage unit 20 and eye drop medication bottles 25, in accordance with some embodiments of the present invention.

FIG. 4B schematically illustrates eye drop bottle storage unit 20 showing the eye drop medication bottles 25 placed within eye drop bottle pods, in accordance with some embodiments of the present invention. Each eye drop bottle may be held in an eye drop bottle pod 205. In the example shown in FIG. 4B, eye drop bottle storage unit 20 may include five eye drop bottle pods respectively denoted 205_1 . . . 205_5, and a controller unit 200. The controller unit 200 is connected to the eye drop bottle pod 205_1, which is connected to eye drop bottle pod 205_2, which is connected to eye drop bottle pod 205_3 and so forth. Each eye drop bottle pod 205 may include indicator light 235. For example, indicator light 205_U may flash at the correct time to indicate to patient 15 to administer eye drops from the eye drop bottle located in eye drop bottle pod 205_5 in accordance with the eye drop administration regime. Each of the eye drop bottle pods may include indicator lights 235 that when flashing indicate to the patient to administer eye drops to the right eye or the left eye (e.g., a right eye indicator light 235_R or a left eye indicator light 235_L) or to both eyes if both indicator lights 235_L and 235_R are flashing.

Figure 5:
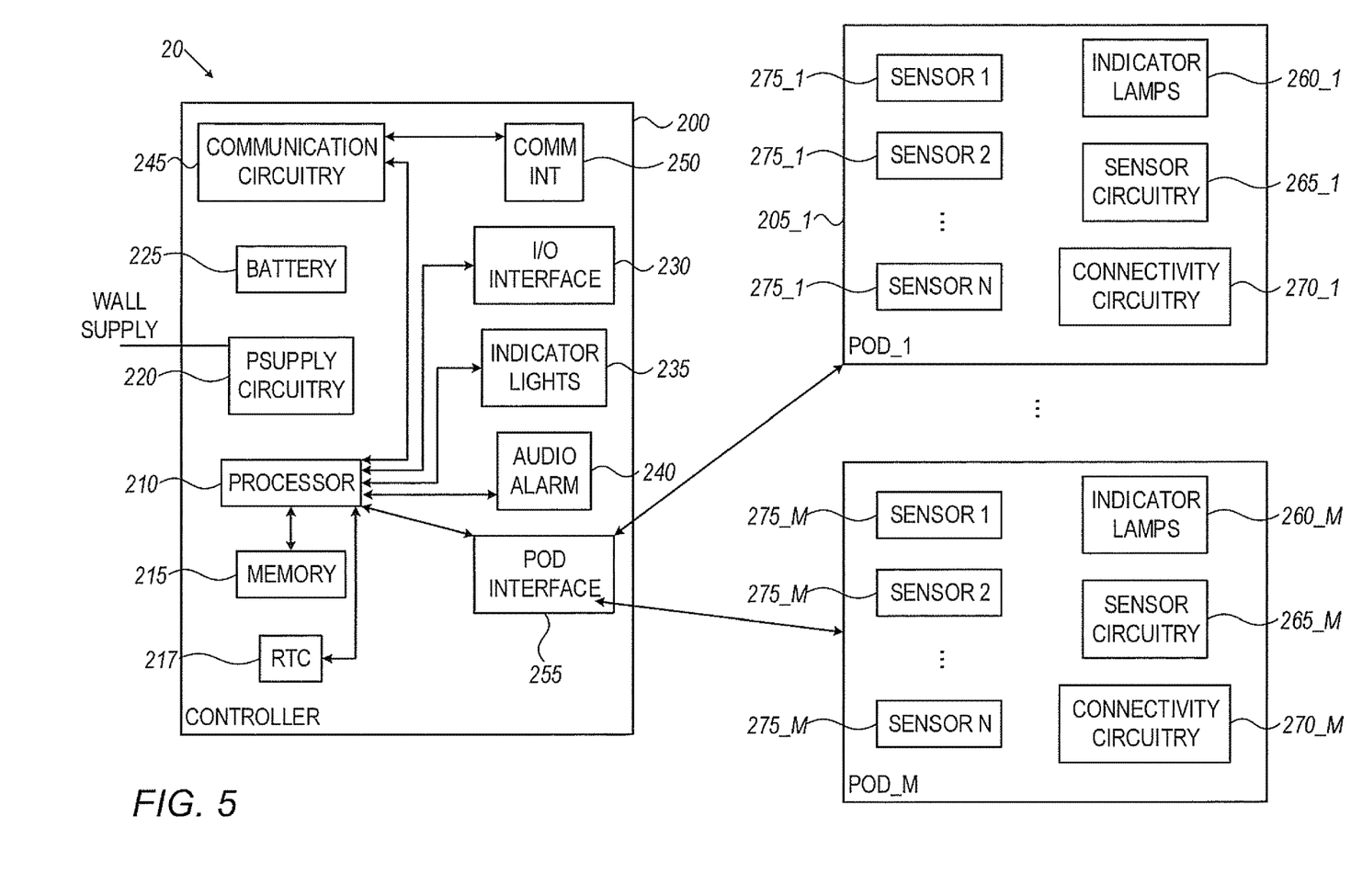
FIG. 5 is a block diagram of an eye drop bottle storage unit, in accordance with some embodiments of the present invention.

FIG. 5 is a block diagram of eye drop bottle storage unit 20, in accordance with some embodiments of the present invention. Controller unit 200 may include a processor 210, a memory 215, a real time clock module (RTC) 217, a battery 225 coupled to power supply circuitry 220, an input/output interface 230, indicator light unit 235, an audio alarm unit 240 (e.g., with a speaker), a communication circuitry unit 245 to communication with server 50 and/or mobile device 32 via a communication interface 250, and pod interface 255 for interfacing with M eye drop bottle pods 205 where M is the integer number of eye drop bottle pods 205. In some embodiments, power supply circuitry 220 may also be powered by mains line voltage (e.g., the wall supply).

In some embodiments of the present invention, the functionality of the block diagram of controller 200 may be realized using a Raspberry Pi Zero W controller unit, for example. (For specifications, see www.raspberrypi.org.) Input/Output (I/O) interface 230 may include a general purpose input output (GPIO). GPIO may be used to control indicator lamps 260, to receive signals from sensors 265, and/or to send an actuating signal to activate the alarm or alert signal.

Battery 225 may include a polymer lithium ion battery. Controller 200 may include a real-time clock module to insure that the unit may possess the real time if controller 200 loses power, e.g., runs of out battery power. Alarm unit 240 may include a piezo buzzer to alert the patient to take their medication. Memory 215 may include a micro SD card (e.g., micro secure digital (SD) card) to store the operating system. I/O interface 230 may include USB port to connect controller 200 to an external computer or mobile device for programming, for example.

Controller unit 200 may be coupled to drive M eye drop bottle pods 205_1 ... 205_M. Eye drop bottle pod 205 may include a one or more sensors 275, indicator lamps 260, sensor circuitry 265 for driving and receiving signals from the sensors, and connectivity circuitry 270 for routing signals between controller 200 coupled to M eye drop bottle pods 205_1 ... 205_M, when each of the eye drop bottle pods may be connected to one another. The signals generated by the one or more sensors 275 may be used to determine whether the eye drop medication bottle was removed from a particular pod, or the volume of medication liquid in the bottle by measuring the position of the surface of the liquid in the bottle before and after use. These signals may be received by processor 210 via connectivity circuitry 270. Using these signals, processor 210 may assess whether the patient is compliant with the patient's personalized eye drop administration regime.

In some embodiments of the present invention, a python script may be running on processor 210 and may gather the received data from sensors 275 to measure patient compliance with the eye drop administration regime. Processor 215 may be configured to sample received data from sensors 275 at predefined times or intervals, such as during medication times or every hour, for example. The python script may use the eye drop administration regime data stored on memory 215 to generate schedules when audio alarm 240 may be activated.

In some embodiments, after the sensors detect that the patient administered the correct eye drop medication, the python script may update the database on memory 215 with a timestamp of the eye drop administration and compliant usage. In some embodiments, after being prompted by audio alarm 240, if the patient has not administered the correct eye drop medication after a predefined duration such as one hour, for example, the database in memory 215 may be updated with the non-compliant event.

The embodiments shown in FIG. 5 are by way of example and not by way of limitation. For example, processor 210 and memory 215 is not limited to a separate controller unit, such as controller 200. Alternatively, processor 210 and memory 215 may be placed in any suitable apparatus for interfacing with one or more eye drop bottle pods 205 such as a separate computer, or other computing device interfaced to one or more eye drop bottle pods 205.

In some embodiments of the present invention, processor 210 and memory 215 may be included in at least one of the one or more eye drop bottle pods. For example, one eye drop bottle pod may comprise circuitry with all or some of the functionality shown in controller 200 of FIG. 5 and may be used to drive and communicate with other eye drop bottle pod, for example, in a chain of modularly connected eye drop bottle pod. In other embodiments, each eye drop bottle pods in the one or said plurality of eye drop bottle pods may include a processor and a memory where the processor in one of the eye drop bottle pods behaves as the master processor controlling the other processors in the remaining eye drop bottle pods.

Figure 6:
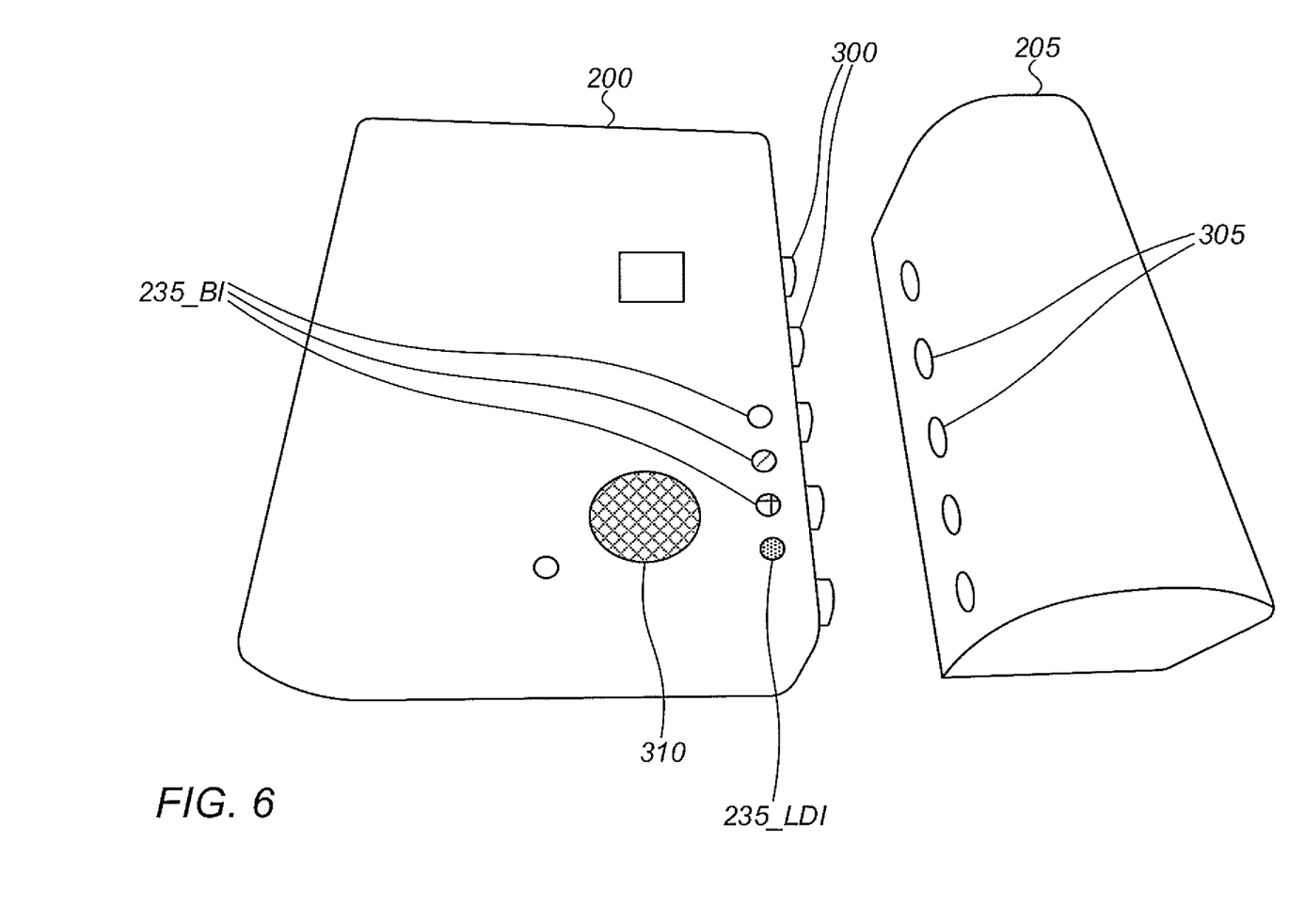
FIG. 6 schematically illustrates a perspective view of a controller unit and an eye drop bottle pod, in accordance with some embodiments of the present invention.

FIG. 6 schematically illustrates a perspective view of controller unit 200 and eye drop bottle pod 205, in accordance with some embodiments of the present invention. Controller 200 may include three battery indicator lights 235_BI to indicate the level of battery charge. In accordance with the eye drop administration regime, when the time arrives to administer eye drops, an audio alarm from a speaker 310 coupled to audio alarm circuitry 240 may be used to alert the patient. If the patient misses administering the eye drops at the proper time, a late dose indication light 235_LDI may be illuminated.

Figure 7:
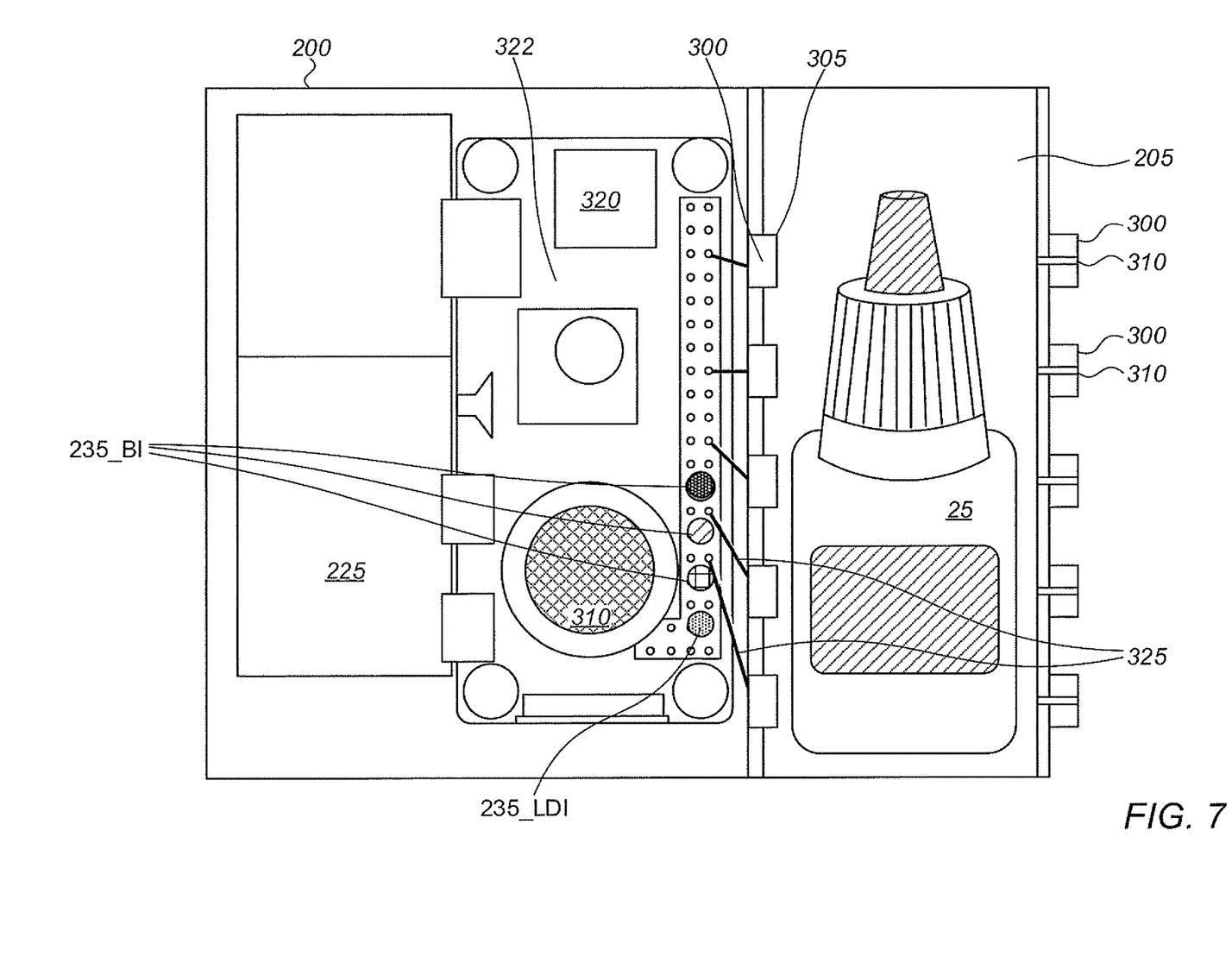
FIG. 7 schematically illustrates a side view of a controller unit connected to an eye drop bottle pod, in accordance with some embodiments of the present invention.

In some embodiments of the present invention, the controller unit housing of controller 200 may include a set of male connectors 300. Similarly, the housing of eye drop bottle pod 205 may include a first set of female connectors 305 on a first side of pod 205 and a second set of male connectors on a second side of pod 205 (not shown in the top view of FIG. 6). The first set of connectors and the second set of connectors may be substantially opposite to one another as shown in FIG. 7. In this manner, two or more eye drop bottle pods 205 may fit together modularly with one another so as to form eye drop bottle storage unit 20 as shown in FIGS. 4A and 4B, for example.

In some embodiments of the present invention, the controller unit housing and/or the housing of eye drop bottle pod 205 may be formed by three-dimensional (3D) printing using poly lactic acid (PLA).

FIG. 7 schematically illustrates a side view of controller unit 200 connected to eye drop bottle pod 205, in accordance with some embodiments of the present invention. Controller 200 is connected to eye drop bottle pod 205 using male connector 300 on controller 200 mated to female connector 305 on eye drop bottle pod 205. Controller 200 may include a printed circuit board card 322, GPIO connectors 320 (e.g., connecting pins 320), a speaker 310 (e.g., piezo buzzer unit). Each of male 300 and female 305 connectors may include holes 310 through which wires and/or conductors may be placed when concatenating multiple eye drop bottle pods 205 together so as to couple the sensors 275, sensor circuitry 265, and indicator lamps 260 in each of the concatenated eye drop bottle pods 205 to controller 200. Interconnects 325 to GPIO 320 may be realized using wires, and/or conducting paint to act as wires and conducting pads, as well as capacitive sensors 275 for the capacitance measurements shown in FIGS. 8A-8B below.

Figures 8A, 8B:
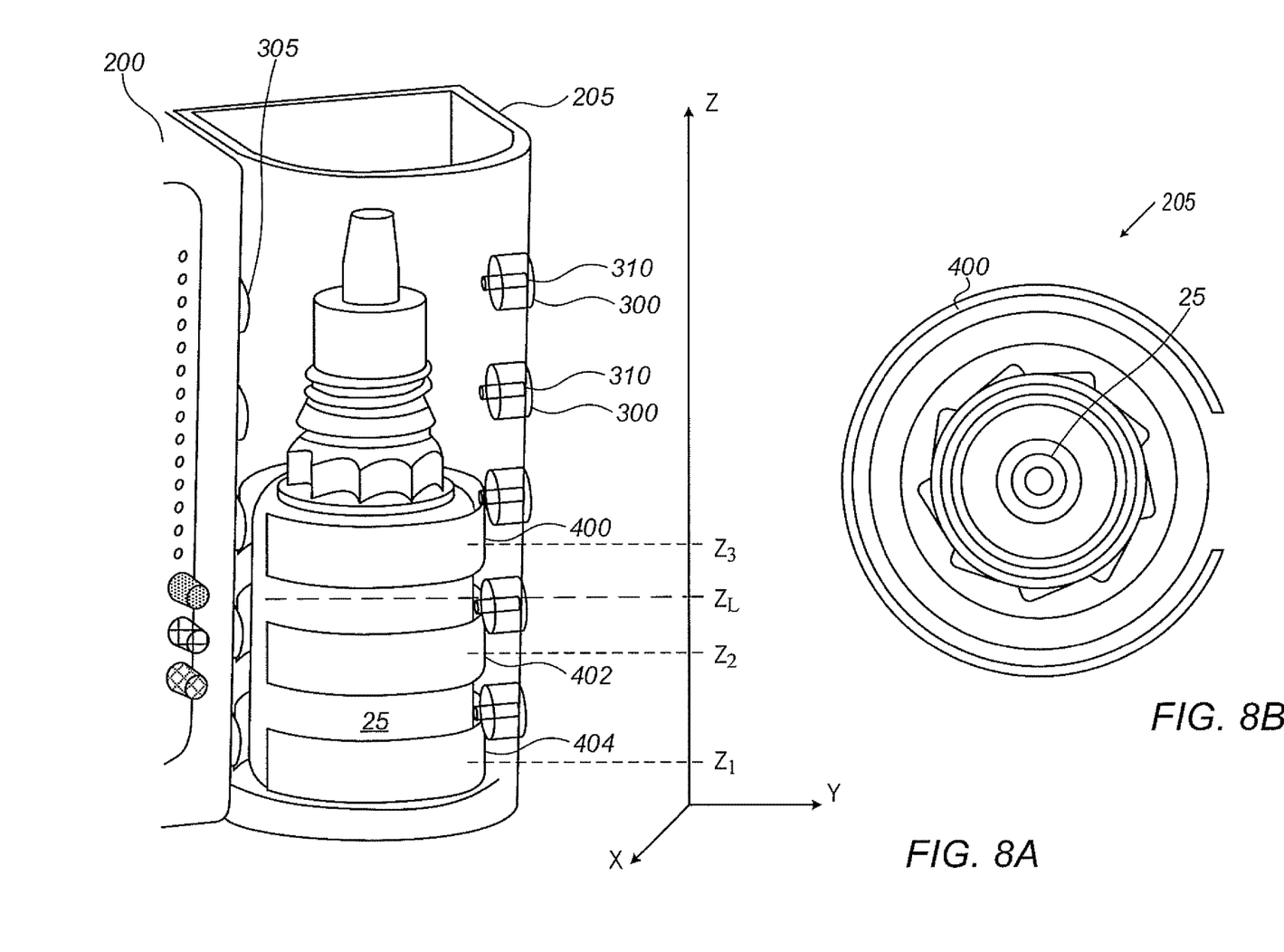
FIG. 8A schematically illustrates a side view of an eye drop bottle pod with capacitive sensors, in accordance with some embodiments of the present invention.
FIG. 8B schematically illustrates a side view of an eye drop bottle pod with a first capacitive ring sensor, in accordance with some embodiments of the present invention.

FIG. 8A schematically illustrates a side view of eye drop bottle pod 205 with capacitive sensors, in accordance with some embodiments of the present invention. The axis passing through the length of eye drop bottle 25 may be aligned with the z-axis for illustrating an exemplary orientation for simplicity. Three capacitive sensors are shown as three capacitive ring sensors—a first capacitive ring sensor 400 at a position $Z_3$ along the z-axis, a second capacitive ring sensor 402 at a position $Z_2$ along the z-axis, and a third capacitive ring sensor 400 at a position $Z_1$ along the z-axis. Predefined positions $Z_1$, $Z_2$ and $Z_3$ may be referenced from the middle of the respective capacitive ring sensor.

FIG. 8B schematically illustrates a side view of eye drop bottle pod 205 showing first capacitive ring sensor 400, in accordance with some embodiments of the present invention.

The capacitive ring sensors may be formed from a conductive paint painted on the wall of interior of eye drop bottle pod 205, so as to form a conductive trace. The eye drop solution may serve as one conductor and the conductive trace may serve as the other conductor. The plastic wall of eye drop bottle 25 may be used as the insulating material to form a capacitor. The conductive trace may be driven by sensor circuitry 265 and the signals may be coupled to controller 200 via connectors 300 and 305. A voltage input such as step voltage waveform, for example, may be applied by sensor circuitry 265 to first capacitive ring sensor 400, second capacitive ring sensor 402, and third capacitive ring sensor 404. Sensor circuitry 265 may include a resistor with the capacitive ring sensors to form an RC circuit. The output waveform from the voltage input, for example, may be then sampled by sensor circuitry 265 and relayed via connectors 300 and 305 to controller 200 for processing by processor 210.

If the capacitive ring sensor surrounds a portion of the eye drop bottle with liquid, the RC time constant of the output waveform will be different than when no liquid is present. A high RC time constant may be measured when liquid is present and a low RC time constant when no liquid is present. Processor 210 may use the received output waveform signals from the three capacitive sensor rings located at predefined positions $Z_1$, $Z_2$ and $Z_3$ to calculate the position $Z_L$ of the height of the liquid in eye drop bottle 25. If the position ZL of the height of the liquid in the eye drop bottle is known prior to and after each administration of eye drops from a given bottle, the change in the volume of the liquid can be used to determine each dosage applied to the eyes of the subject (e.g., the number of eye drops administered) and whether the subject is complaint with the eye drop administration regime for each application of eye drops.

In some embodiments of the present invention, one capacitive ring sensor (not shown in FIG. 8A) may be used to calculate the position $Z_L$ of the height of the liquid in eye drop bottle 25 instead of the three separate ring sensors at predefined positions $Z_1$, $Z_2$ and $Z_3$ as shown in FIG. 8A. The one capacitive ring sensor may be configured to cylindrically wrap entirely around the length of eye drop bottle 25 along the z-axis. Additionally, the one capacitive ring sensor may include a gap along the z-axis so as to form two half cylindrical capacitive plates around eye drop bottle 25 and oriented along the z-axis so as to permit driving each separate plate with different voltages from sensor circuitry 265, typically voltages of opposite polarity.

Figure 9:
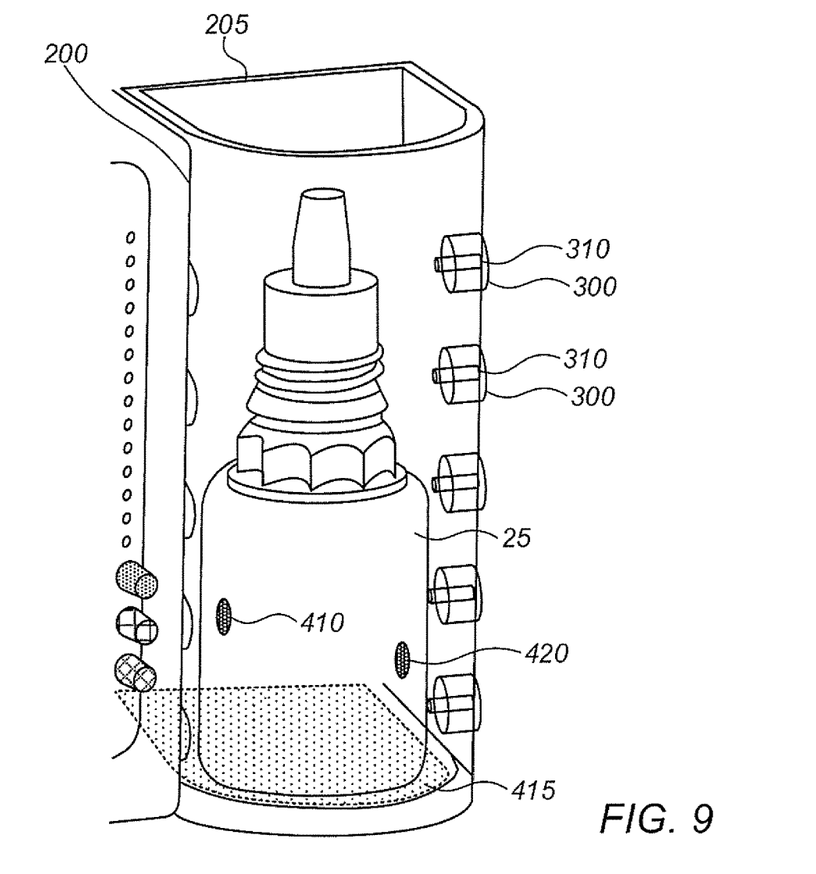
FIG. 9 schematically illustrates a side view of an eye drop bottle pod with different sensor types, in accordance with some embodiments of the present invention.

FIG. 9 schematically illustrates a side view of eye drop bottle pod 205 with different sensor types, in accordance with some embodiments of the present invention. In some embodiments, to determine the presence or the absence of eye drop bottle 25 in eye drop bottle pod 205, a weight sensor 415 may be attached to the bottom of eye drop bottle pod 205. Weight sensor 415 may also be used to detect the residual amount of eye drop medication remaining in eye drop bottle 25.

Other sensors to detect the presence of eye drop bottle 25 may include a piezo element for pressure sensing, an infrared proximity sensor including an infrared light emitting diode and a photoelectric receiver, and an ultrasonic sensor to detect echoes so as to measure the distance to the eye drop bottle 25 (e.g., to detect if eye drop bottle 25 is present). A thermal sensor 420 may be configured to be placed on the walls of eye drop bottle 25 to detect heat/pressure from the subject's fingers during eye drop administration. Thermal sensor 420 may be used to detect the presence of eye drop bottle 25. In some embodiments, a pressure sensor may be placed into the wall of eye drop bottle 25, so as to determine the number of squeezes made on the bottle to extract eye drops.

In some embodiments of the present invention, a radio frequency scanner sensor or Barcode scanner sensor may be placed in the eye drop bottle pod 205 to detect the id of the eye drop bottle 25 identifying the eye drop medication in the bottle.

In some embodiments of the present invention, eye drop bottle pod 205 may include a lid with a mechanical lock or latch (not shown in the figures) and may be used to detect the number of times that the eye drop bottles are taken out for use and/or detect the number of times that the lids are opened. Moreover, the mechanical lock may prevent the subject from administering the wrong eye drop medication at a given time.

Figure 10:
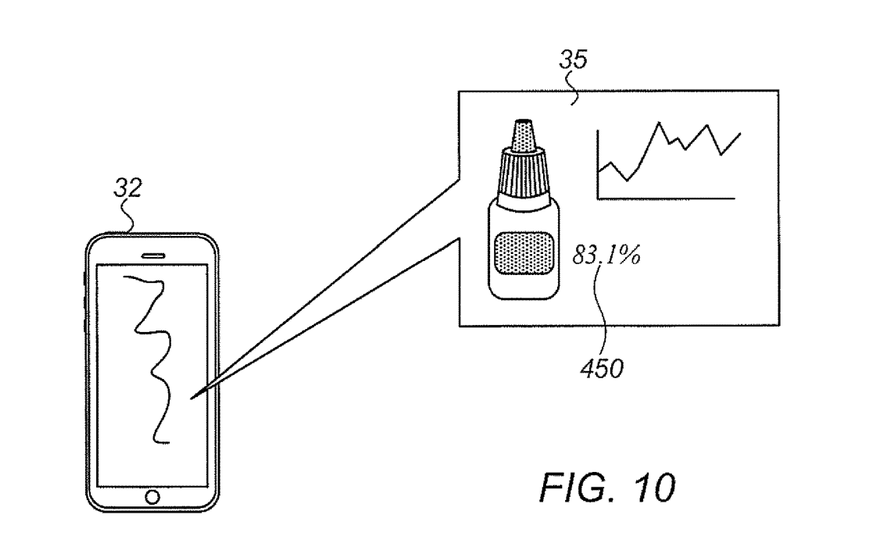
FIG. 10 schematically illustrates an eye drop administration compliance application operating on a mobile device, in accordance with some embodiments of the present invention.

FIG. 10 schematically illustrates eye drop administration compliance application 35 operating on mobile device 32, in accordance with some embodiments of the present invention. Eye drop administration compliance application 35 on mobile device 32 may be configured to communicate with eye drop bottle storage unit 20 and to receive from eye drop bottle storage unit 20 information about the administration of eye drops by the subject from each eye drop bottle held in each eye drop bottle pod in eye drop bottle storage unit 20. For example, eye drop administration compliance application 35 may be configured to display a compliance factor 450. Eye drop administration compliance application 35 may also be used on desktop computer, tablet, or any suitable device through a hot spot generated by eye drop bottle storage unit 20.

In some embodiments of the present invention, an eye drop bottle storage unit for eye drop administration compliance may include a memory, a processor, and one or a plurality of eye drop bottle pods, where each eye drop bottle pod of the one or said plurality of eye drop bottle pods is configured to hold an eye drop bottle, and may include one or a plurality of sensors. The memory may be configured to store data of an eye drop administration regime of a subject. The processor may be configured to receive signals from the one or said plurality of sensors of each eye drop bottle pod, and to determine from the received signals whether the subject administered eye drops into eyes of the subject from each eye drop bottle respectively held in each eye drop bottle pod of the one or said plurality of eye drop bottle pods in accordance with the eye drop administration regime data.

In some embodiments of the present invention, the one or plurality of sensors comprise capacitive sensors may be placed at predefined positions along the length of each eye drop bottle in each eye drop bottle pod where the processor may be configured to determine whether the subject administered eye drops from each eye drop bottle by computing a height of a liquid in each eye drop bottle using capacitance measurements computed from the signals received from the capacitive ring sensors.

In some embodiments of the present invention, the processor may be configured to compute a compliance factor and to assess whether the subject is complying with the eye drop administration regime when the compliance factor is greater than a predefined threshold.

In some embodiments of the present invention, a method for eye drop administration compliance may include in a memory, storing data of an eye drop administration regime of a subject. In a processor, signals may be received from one or a plurality of sensors from one or plurality of eye drop bottle pods, where each eye drop bottle pod from the one or said plurality of eye drop bottle pods is configured to hold an eye drop bottle. The received signals may be used to determine whether the subject administered eye drops into eyes of the subject from each eye drop bottle respectively held in each eye drop bottle pod of the one or said plurality of eye drop bottle pods in accordance with the eye drop administration regime data.

In some embodiments of the present invention, sensor 275 may be selected from the group consisting of a capacitive sensor, a pressure sensor, a thermal sensor, a weight sensor, a Radio Frequency identification (RFID) tag scanner, a bar code scanner, a piezoelectric element for pressure sensing, an infrared proximity sensor, and an ultrasonic sensor.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An eye drop bottle storage unit for eye drop administration compliance, the eye drop bottle storage unit comprising:
one or a plurality of eye drop bottle pods, wherein each eye drop bottle pod of the one or said plurality of eye drop bottle pods is configured to hold an eye drop bottle, and comprises one or a plurality of capacitive sensors, and a housing with a first set of connectors on a first side of the housing and a second set of connectors on a second side of the housing;
a memory configured to store data of an eye drop administration regime of a subject; and
a processor configured to receive signals from the one or said plurality of capacitive sensors of each eye drop bottle pod, and to determine from the received signals whether the subject administered eye drops into eyes of the subject from each eye drop bottle respectively held in each eye drop bottle pod of the one or said plurality of eye drop bottle pods in accordance with the eye drop administration regime data by computing change in the volume of a liquid in each eye drop bottle using capacitance measurements computed from the signals received from the one or said plurality of capacitive sensors.

2. The eye drop bottle storage unit according to claim 1, wherein the processor is configured to compute a compliance factor and to assess whether the subject is complying with the eye drop administration regime when the compliance factor is greater than a predefined threshold.

3. The eye drop bottle storage unit according to claim 1, further comprising a controller unit including the processor and the memory.

4. The eye drop bottle storage unit according to claim 1, wherein at least one of the one or said plurality of eye drop bottle pods includes the processor.

5. The eye drop bottle storage unit according to claim 1, wherein the one or the plurality of capacitive sensors is a capacitive ring sensor forming two half cylindrical capacitive plates around the eye drop bottle.

6. The eye drop bottle storage unit according to claim 1, further comprising indicator lights to indicate to the subject to administer eye drops from the eye drop bottle into a right eye or a left eye.

7. The eye drop bottle storage unit according to claim 1, wherein the processor is configured to relay the computed change in the volume of the liquid in each eye drop bottle to a mobile device.

8. The eye drop bottle storage unit according to claim 1, further comprising communication circuitry configured to relay information to a server or a mobile device about the administration of eye drops by the subject from each eye drop bottle held in each eye drop bottle pod in the one or said plurality of eye drop bottle pods.

9. The eye drop bottle storage unit according to claim 1, further comprising a real time clock, and wherein the processor is configured to assess, using the real time clock, when the subject needs to administer eye drops from each eye drop bottle held in each eye drop bottle pod in the one or said plurality of eye drop bottle pods.

10. The eye drop bottle storage unit according to claim 1, further comprising an alarm configured to alert the subject to administer eye drops.

11. The eye drop bottle storage unit according to claim 1, further comprising indicator lights configured to indicate to the subject from which eye drop bottle to administer eye drops.

12. The eye drop bottle storage unit according to claim 1, further comprising one or a plurality of additional sensors selected from the group consisting of a pressure sensor, a thermal sensor, a weight sensor, a Radio frequency identification (RFID) tag scanner, a bar code scanner, a piezoelectric element for pressure sensing, an infrared proximity sensor, and an ultrasonic sensor.

13. The eye drop bottle storage unit according to claim 1, wherein the first set of connectors on the first side of the housing and the second set of connectors on the second side of the housing are substantially opposite to one another.

14. The eye drop bottle storage unit according to claim 1, wherein each eye drop bottle pods from said plurality of eye drop bottle pods are configured to fit together modularly with one another.

15. The eye drop bottle storage unit according to claim 1, wherein the one or said plurality capacitive sensors are configured to cylindrically wrap around the length of the eye drop bottle.

16. A method for eye drop administration compliance, comprising:
storing, in a memory, data of an eye drop administration regime of a subject;
receiving, in a processor, signals from one or a plurality of capacitive sensors from one or a plurality of eye drop bottle pods, wherein each eye drop bottle pod from the one or said plurality of eye drop bottle pods is configured to hold an eye drop bottle, and comprises a housing with a first set of connectors on a first side of the housing and a second set of connectors on a second side of the housing; and
determining, in the processor, from the received signals whether the subject administered eye drops into eyes of the subject from each eye drop bottle respectively held in each eye drop bottle pod of the one or said plurality of eye drop bottle pods in accordance with the eye drop administration regime data by computing change in the volume of a liquid in each eye drop bottle using capacitance measurements computed from the signals received from the one or said plurality of capacitive sensors.

17. The method according to claim 16, wherein the one or the plurality of capacitive sensors is a capacitive ring sensor forming two half cylindrical capacitive plates around the eye drop bottle.

18. The method according to claim 16, further comprising indicating to the subject, by means of indicator lights of the one or said plurality of eye drop bottle pods, to administer eye drops from the eye drop bottle into a right eye or a left eye.

19. The method according to claim 4, further comprising relaying the computed change in the volume of the liquid in each eye drop bottle to a mobile device.

20. The method according to claim 19, further comprising automatically ordering, from the mobile device, a new eye drop bottle when the volume of the liquid is less than a predefined threshold.

21. The method according to claim 16, further comprising computing a compliance factor and assessing whether the subject is complying with the eye drop administration regime when the compliance factor is greater than a predefined threshold.

22. The method according to claim 21, further comprising recomputing the compliance factor in predefined intervals.

23. The method according to claim 16, further comprising relaying information to a mobile device about whether the subject is complying with the eye drop administration regime.

24. The method according to claim 23, wherein the information comprises medication compliance rates.

25. The method according to claim 16, further comprising relaying information to a server or to a mobile device about the administration of eye drops by the subject from each eye drop bottle held in each eye drop bottle pod in the one or said plurality of eye drop bottle pods.

26. The method according to claim 16, further comprising assessing, using a real time clock, when the subject needs to administer eye drops from each eye drop bottle held in each eye drop bottle pod in the one or said plurality of eye drop bottle pods.

27. The method according to claim 4, further comprising alerting the subject with an alarm to administer eye drops.

28. The method according to claim 16, further comprising indicating to the subject with the indicator lights of the one or said plurality of eye drop bottle pods from which eye drop bottle to administer eye drops.

29. A system for eye drop administration compliance, comprising:
an eye drop bottle storage unit, comprising:
one or a plurality of eye drop bottle pods, wherein each eye drop bottle pod of the one or said plurality of eye drop bottle pods is configured to hold an eye drop bottle, and comprises one or a plurality of capacitive sensors, and a housing with a first set of connectors on a first side of the housing and a second set of connectors on a second side of the housing;
a memory configured to store data of an eye drop administration regime of a subject;
communication circuitry to relay information about an administration of eye drops by the subject; and
a processor configured to receive signals from the one or said plurality of capacitive sensors of each eye drop bottle pod, and to determine from the received signals whether the subject administered eye drops into eyes of the subject from each eye drop bottle respectively held in each eye drop bottle pod of the one or said plurality of eye drop bottle pods in accordance with the eye drop administration regime data by computing change in the volume of a liquid in each eye drop bottle using capacitance measurements computed from the signals received from the one or said plurality of capacitive sensors; and
wherein the system further comprising a server, configured to receive the information relayed from the communication circuitry, wherein the server comprising:
a server communication module configured to communicate with a communication module of the eye drop bottle storage unit; and
a server processor configured to receive input data from a health care professional, to generate the eye drop administration regime of the subject based on the input data, to relay the eye drop administration regime of the subject to the eye drop bottle storage unit via the server communication module.

30. The system according to claim 29, wherein the eye drop bottle storage unit further comprising indicator lights to indicate to a subject to administer eye drops from the eye drop bottle into a right eye or a left eye.

31. The system according to claim 29, wherein the server processor is configured to generate a personalized medication card for the subject based on the input data.

32. The system according to claim 29, wherein the processor is configured to relay the information to the health care professional via the communication circuitry about whether the subject administered eye drops from each eye drop bottle in accordance with the eye drop administration regime data.

* * * * *